United States Patent
Sinn et al.

(10) Patent No.: US 6,706,713 B1
(45) Date of Patent: Mar. 16, 2004

(54) CONJUGATE FOR TREATING INFLAMMATORY INFECTIOUS AND/OR SKIN DISEASES

(75) Inventors: Hansjörg Sinn, Wiesloch (DE); Hans-Hermann Schrenk, Zeiskamm (DE); Wolfgang Maier-Borst, Dossenheim (DE); Gerd Stehle, Jahnstrasse 1, D-89584 Ehingen (DE)

(73) Assignees: Deutsches Krebsforschungszentrum Stiftung des Offentlichen Rechts, Heidelberg (DE); Gerd Stehle, Ehingen (DE)

( * ) Notice: Subject to any disclaimer, the term of this patent is extended or adjusted under 35 U.S.C. 154(b) by 0 days.

(21) Appl. No.: 08/949,592

(22) PCT Filed: Apr. 12, 1996

(86) PCT No.: PCT/DE96/00644

§ 371 (c)(1),
(2), (4) Date: Oct. 14, 1997

(87) PCT Pub. No.: WO96/32133

PCT Pub. Date: Oct. 17, 1996

(30) Foreign Application Priority Data

Apr. 13, 1995 (DE) .......................................... 195 14 088

(51) Int. Cl.[7] .............................................. A61K 31/495
(52) U.S. Cl. .................. 514/249; 424/1.69; 424/9.6; 424/9.61; 424/1.53; 514/34; 514/152; 514/224.2; 514/676; 514/680; 514/681; 514/683
(58) Field of Search ................... 424/1.69, 9.6, 424/9.61, 1.53; 514/224.2, 152, 680, 681, 34, 676, 683, 249

(56) References Cited

U.S. PATENT DOCUMENTS

| | | | | |
|---|---|---|---|---|
| 4,767,745 A | * | 8/1988 | Young et al. .................. 514/21 |
| 4,926,869 A | * | 5/1990 | Rubin et al. .................. 128/654 |
| 5,051,406 A | * | 9/1991 | Satoh .......................... 514/21 |
| 5,171,749 A | * | 12/1992 | Levy et al. .................. 514/410 |

FOREIGN PATENT DOCUMENTS

| | | | |
|---|---|---|---|
| EP | 0 282 057 | | 9/1988 |
| EP | 0326618 | * | 8/1989 |
| EP | 0 326 618 | | 8/1989 |
| EP | 0 352 076 | | 1/1990 |
| EP | 0352076 | * | 1/1990 |
| EP | 0601183 | * | 6/1994 |
| EP | 0 601 183 | | 6/1994 |
| EP | 0 649 857 | | 4/1995 |
| JP | 63 267 734 | | 11/1988 |
| JP | 63267734 | * | 11/1988 |
| WO | WO 87/04351 | | 7/1987 |
| WO | WO 93/23743 | | 11/1993 |
| WO | WO 95/12414 | | 5/1995 |

OTHER PUBLICATIONS

The Use of Protein—pp. 329–342, Aurej et al in Neoplasma 35, 3, 1988.*
Goldenberg H, Abstract of WO9404702, 3/94.*
Byres et al, Neoplasma, 35(3) 329–42, 88.*
Chem Abstracts vol. 124 #6,5 # 66584, Mukhopadhyay et al. A Process for the Preparation—2/96.*
Int. J. of Radiation—Bd. 18, Nr. 6, Thakur et al. Technetium–99–m–labelled Proteins—Jan. 1, 1991.*
J. of Fluorescence Bd. 3, Nr. 3, Terpetshnig et al. An Investigation of Squarainers—Sep. 1, 1993.*
J. of Pharmaceutical Sciences Bd. 66, Nr. 3, Hare et al., Analysis of Sulindac & Metabolites—3/77.*

(List continued on next page.)

Primary Examiner—Neil S. Levy
(74) Attorney, Agent, or Firm—Pennie & Edmonds LLP

(57) ABSTRACT

This invention relates to the use of a conjugate comprising an active substance and a native protein which is not recognized as foreign protein for the production of a pharmaceutical preparation for treating and/or diagnosing inflammatory, infectious and/or skin diseases.

14 Claims, 1 Drawing Sheet

OTHER PUBLICATIONS

Figure 1:
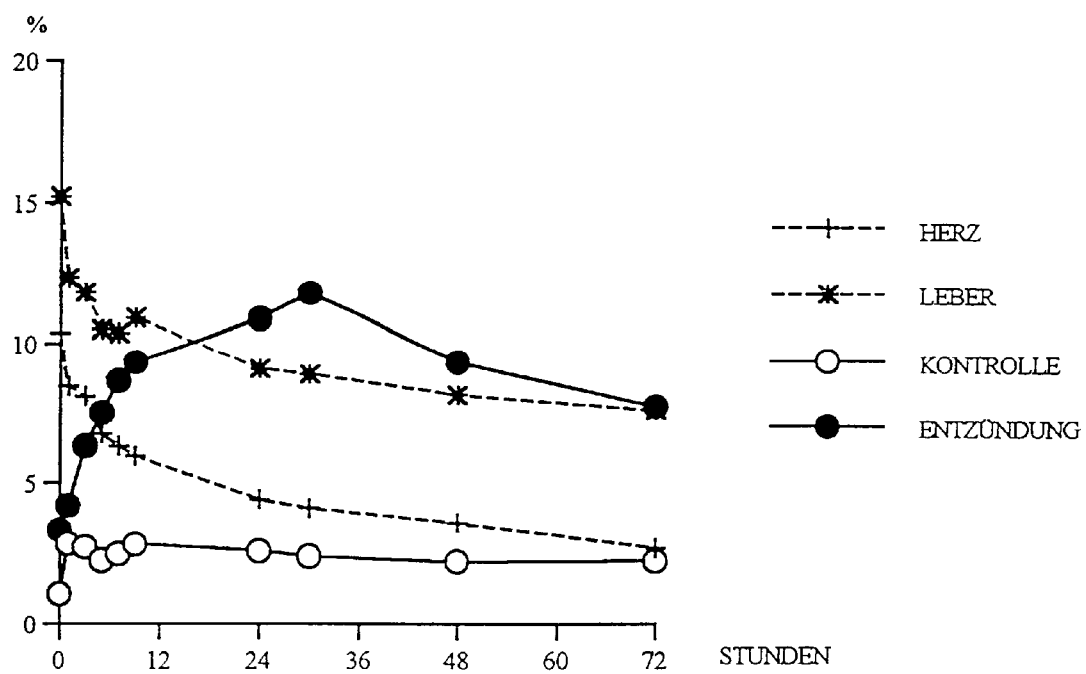

Mukhopadhyay et al., 1989, "Receptor–Mediated Drug Delivery to Macrophages in Chemotherapy of Leishmaniasis," *Science 244*: 705–707.

Weinblatt, 1995, "Methotrexate for Chronic Diseases in Adults," *The New England Journal of Medicine 332*(5):330–331.

\* cited by examiner

CONJUGATE FOR TREATING INFLAMMATORY INFECTIOUS AND/OR SKIN DISEASES

This is a national phase filing of the Application No. PCT/DE96/00644, which was filed with the Patent Corporation Treaty on Apr. 12, 1996, and is entitled to priority of the German Patent Application 195 14 088.5, filed Apr. 13, 1995.

I. FIELD OF THE INVENTION

This invention relates to a conjugate comprising an active substance and a native protein which is not recognized as a foreign protein, for the production of a pharmaceutical preparation for treating and/or diagnosing inflammatory, infectious and/or skin diseases.

II. BACKGROUND OF THE INVENTION

Up to the present, pharmaceutical preparations have been used for treating inflammatory, infectious and skin diseases, which are administered in high doses, partially even several times daily. In addition, these pharmaceutical preparations accumulate in many tissues. Thus, they are a major load for the body.

DE-A-41 22 210 discloses a conjugate consisting of a tumor-active compound and a native protein which is not recognized as a foreign protein. This conjugate is used for treating tumor diseases.

Surprisingly, it has now turned out that such a conjugate is also suitable for treating and/or diagnosing inflammatory, infectious and/or skin diseases, the drawbacks of the pharmaceutical preparations, used for this purpose up to the present, not occurring.

III. SUMMARY OF THE INVENTION

This invention relates to the use of a conjugate comprising an active substance and a native protein which is not recognized as foreign protein for the production of a pharmaceutical preparation for treating and/or diagnosing inflammatory, infectious and/or skin diseases.

IV. BRIEF DESCRIPTION OF THE DRAWINGS

FIG. 1 shows the scintigraphic detection of an uptake of radioactively labeled MTX-HSA in an inflammation.

V. DETAILED DESCRIPTION OF THE INVENTION

According to the present invention a conjugate consisting of a tumor-active compound and a native protein which is not recognized as a foreign protein (see, DE-A-41 22 210) is used for the production of a pharmaceutical preparation for treating and/or diagnosing inflammatory, infectious and/or skin diseases such as psoriasis.

The expression "active substance" comprises compounds of any kind, which can be used for treating and/or diagnosing inflammatory, infectious and/or skin diseases. Examples of such compounds are photoactive compounds and chemotherapeutic agents. Examples of photoactive compounds are porphins such as o-, n-, and/or p-tetracarboxyphenyl porphines chlorins, bacteriochlorins, phthalocyanines and derivatives thereof. The photoactive compounds may optionally include a metal and/or a metal ion. Examples of chemotherapeutic agents are cytostatic agents and antibiotics. Representatives thereof are, e.g., doxorubicin, daunorubicin, tetracyclines, antraquinone-2-carboxylic acid, carminic acid, platinum complexes and methotrexate (MTX).

The above compounds may be labeled detectably. This may be effected, e.g., by means of a radioactive substance such as iodine. It is also favorable for the above compounds to have an acid function, e.g., a carboxyl group. This facilitates their bonding to the "protein".

One or more of the above compounds may be present in a conjugate used according to the invention. If several compounds are present, they may be the same or differ from one another.

The expression "protein" comprises proteins of any kind, which are suitable to enrich above compounds linked therewith in cells or tissues which are affected with the above diseases. Examples of such proteins are those proteins that have a molecular weight up to 90,000 dalton such as albumin, especially human serum albumin (HSA), and transferrin.

Conjugates used according to the invention may be produced according to conventional methods. For example, the production may be carried out according to the process described in DE-A-41 22 210.

Conjugates used according to the invention distinguish themselves by accumulating in cells and tissues which are affected with inflammatory processes. Therefore, minor doses of these conjugates suffice to treat such processes, which minimizes the load for the body. Hence the conjugates used according to the invention are suited in the best possible way to treat and/or diagnose inflammatory, infectious and/or skin diseases.

The below example explains the invention in more detail. The following preparations and example are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

VI. EXAMPLES

A. Example 1

Uptake of Radioactively Labeled MTX-HSA in an Inflammation at the Leg of a Rat

An inflammation was produced as usual in a rat's leg by injection of sephadex beads. Then, the rat was given the radioactively labeled conjugate MTX-HSA according to the invention. MTX-HSA was determined scintigraphically in the inflamed leg, the non-inflamed leg (as control) as well as the heart and liver regions.

As follows from FIG. 1, the conjugate MTX-HSA according to the invention accumulates in the inflamed leg.

All references cited within the body of the instant specification are hereby incorporated by reference in their entirety.

What is claimed is:

1. A method of diagnosing an inflammatory disease comprising administering a pharmaceutical composition comprising a conjugate and a pharmaceutically acceptable carrier, said conjugate comprising:

(a) an active substance selected from the group consisting of porphines, chlorins, bacteriochlorins, phthalocyanines, doxorubicin, daunorubicin, tetracyclines, anthraquinone-2-carboxylic acid, carminic acid and methotrexate; and (b) albumin, wherein the active substance is covalently bound to the albumin, and the albumin is in its native form.

2. The method of claim 1 wherein the conjugate comprises a plurality of active substances covalently bound to the albumin.

3. The method of claim 1 wherein the active substance is detectably labeled.

4. The method of claim 3 wherein the active substance is radioactively labeled.

5. A method of treating an inflammatory disease comprising administering a pharmaceutical composition comprising a conjugate and a pharmaceutically acceptable carrier, said conjugate comprising:

(a) an active substance selected from the group consisting of porphines, chlorins, bacteriochlorins, phthalocyanines, doxorubicin, daunorubicin, tetracyclines, anthraquinone-2-carboxylic acid, carminic acid and methotrexate; and (b) albumin, wherein the active substance is covalently bound to the albumin, and the albumin is in its native form.

6. The method of claim 5 wherein the conjugate comprises a plurality of active substances covalently bound to the albumin.

7. The method of claim 5 wherein the active substance is detectably labeled.

8. The method of claim 7 wherein the active substance is radioactively labeled.

9. A method of diagnosing an inflammatory disease comprising administering a pharmaceutical composition, said pharmaceutical composition comprising a conjugate and a pharmaceutically acceptable carrier, said conjugate comprising methotrexate covalently bound to albumin, wherein the albumin is in its native form.

10. The method of claim 9 wherein the methotrexate is detectably labeled.

11. The method of claim 10 wherein the methotrexate is radioactively labeled.

12. A method of treating an inflammatory disease comprising administering a pharmaceutical composition, said pharmaceutical composition comprising a conjugate and a pharmaceutically acceptable carrier, said conjugate comprising methotrexate covalently bound to albumin, wherein the albumin is in its native form.

13. The method of claim 12 wherein the methotrexate is detectably labeled.

14. The method of claim 13 wherein the methotrexate is radioactively labeled.

* * * * *